United States Patent [19]

Lord

[11] Patent Number: 4,623,349
[45] Date of Patent: Nov. 18, 1986

[54] OSTEAL PROSTHESIS AND THE PRODUCTION THEREOF

[76] Inventor: Gerald Lord, 4, rue Thiers, 75116 Paris, France

[21] Appl. No.: 508,041

[22] Filed: Jun. 27, 1983

[30] Foreign Application Priority Data

Jun. 29, 1982 [FR] France ............................ 82 11412

[51] Int. Cl.$^4$ .............................................. A61F 2/30
[52] U.S. Cl. .................................................... 623/18
[58] Field of Search ..................... 3/1, 1.9, 1.91, 1.911, 3/1.912, 1.913; 128/92 C, 92 CA

[56] References Cited

U.S. PATENT DOCUMENTS 4,430,761 2/1984 Niederer et al. ............... 128/92 CA

FOREIGN PATENT DOCUMENTS 2551013 5/1976 Fed. Rep. of Germany ....... 3/1.913
989341 9/1951 France ................................. 3/1.913
2069340 8/1981 United Kingdom ................ 3/1.913

Primary Examiner—Richard J. Apley
Assistant Examiner—David J. Isabella
Attorney, Agent, or Firm—Oblon, Fisher, Spivak, McClelland & Maier

[57] ABSTRACT

An osteal prosthesis having an outer surface splined in a direction generally parallel to its mean axis is capable of being secured in the bone without cement, the bone tissue developing so as to at least partly occupy the interior or hollow between the splines.

The cross-sectional profile of the splines is such that it imparts a bone tissue retaining capability, and the longitudinal interior surface or hollow of the splines, which are non-cylindrical, has a shape which tapers from the end of the prosthesis (lower end) which is the most deeply embedded in the bone to the other end (upper end), the prosthesis being thus capable of being extracted from the bone tissue by a tractive movement.

6 Claims, 8 Drawing Figures

4,623,349

OSTEAL PROSTHESIS AND THE PRODUCTION THEREOF

BACKGROUND OF THE INVENTION

The present invention relates to the field of osteal prostheses. The object of the invention is to provide a new prosthesis and a method for producing the latter.

The general technique of implanting metal parts for replacing or consolidating bones or osteal articulations is already known. Of course, the shape of the implant must be adapted to the concerned bone part. This is for example the case of prostheses adapted for the articulations of the hip or knee.

Metal implants were first employed fixed in the living bone by a cement, in particular a cement based on acrylic resin. This fixing technique employing cement results in many drawbacks, among which may be mentioned a defective performance of the prosthesis owing to risk of the cement breaking up and intolerance on the part of the organism and the bone tissue of the foreign body formed by the cement.

This is why prostheses were proposed, the securing of which did not require the use of cement. For this purpose, the surface of the implant was rendered rough or porous so as to permit the development or growth of the bone tissue on the surface of the prosthesis itself and thereby ensure its anchoring in the bone. The drawbacks of the technique of securing with cement are practically completely eliminated by this technique, but the latter may be still further improved. By way of illustration, it may be estimated that the use of cement results, in the case of hip prostheses, in more than 25% of failures owing to the loosening of the implant in the bone. This percentage of failures is substantially reduced when a porous or rough surface is provided on the implant, but in at least 10% of the cases it is necessary for many various reasons to intervene surgically again in order to replace the prosthesis. But, in this case, the prosthesis cannot be simply extracted, since, owing to the extremely strong anchoring effect created by the development or growth of the bone tissue, a delicate surgical intervention is necessary with a cutting of the bone in order to remove and replace the prosthesis.

By way of the prior documents illustrating the prior art, there may be mentioned German Pat. No. 837,294, French Pat. No. 72,27,966 (publication No. 2,194,123), U.S. Pat. No. 3,905,047 and French patent application published under No. 2,356,465. The teaching of these various patents may be briefly summarized as follows.

German Pat. No. 837,294 relates to a prosthesis whose shaft (or stem) has an outer surface which is splined generally in a direction parallel to the mean axis. No precise information is given concerning the splines which may have any shape, number and size. Further, their profile may have an acute angle or be rounded. In fact, these splines cannot ensure a sufficient retaining effect on the part of the bone tissue and, moreover, the rectilinear longitudinal profile of these spline does not allow an extraction of the prosthesis stem under satisfactory conditions.

French Pat. No. 72,27,966 (publication No. 2,194,123) proposes a prosthesis adapted to be secured without cement and comprising a porous outer surface. Once placed in position, such a prosthesis cannot be extracted. Further, the conditions under which such a prosthesis is obtained result in a risk of corrosion of the surface. The latter is also rendered more fragile which, under the effects of the high stresses, may create weak zones and finally result in the fracture of the prosthesis.

U.S. Pat. No. 3,905,047 concerns a prosthesis having surface irregularities. Once placed in position, such a prosthesis cannot be extracted by a simple tractive force owing to the development of the bone tissue, which constitutes one of the features claimed by the patent.

French patent application published under No. 2,356,465 relates in particular to a prosthesis comprising on its outer surface a covering constituted by balls or spherules. The latter are distributed in a random manner so as to ensure a solid anchoring effect. Such a prosthesis cannot be extracted in the case of an accident without a special surgical intervention.

Therefore, at the present time there are clearly no osteal prostheses to the knowledge of the applicant which may be secured in position without cement, which are capable of being effectively retained in the bone tissue after development of the latter and yet which may be extracted, if required, without the obligation to effect a delicate surgical intervention.

SUMMARY OF THE INVENTION

An object of the invention is to provide a new prosthesis which simultaneously satisfies all these requirements.

Another object of the invention is to produce such a prosthesis under industrial conditions which result in a product having a strength much higher than that of known prostheses. In particular, the production method results in no weakening of the surface of the prosthesis.

Broadly, the invention provides an osteal prosthesis which has an outer surface splined in a direction generally paralel to its mean axis and is capable of being secured without cement, the bone tissue developing so as to occupy at least partly the interior of the splines, said prosthesis being characterized in that simultaneously the profile (cross-section) of the splines is such that it imparts a bone tissue-retaining capability, and the longitudinal troughs of the splines, which are non-cylindrical, have a shape which tapers from the end of the prosthesis (lower end) which is the most deeply inserted in the bone to the other end (upper end), so that the prosthesis is capable of being extracted from the bone tissue by a tractive movement.

The prosthesis according to the invention is an improvement of the subject matter of German Pat. No. 837,294 in that it affords, in combination, the desired anchoring effect for the bone tissue and the possibility of extraction.

The cross-sectional profile of the splines must impart a high bone tissue-retaining capability. In contrast to the teaching of German Pat. No. 837,294, this profile therefore must not be open but include, at least partly, a narrowed part, so that the developing bone tissue may be trapped in the bottom of the splines. For this purpose, the cross-sectional profile may be curvilinear or circular or a combination of these two types of profile it being possible to interconnect the arcs by rectilinear parts. In combination with this cross-sectional profile the splines formed on the outer surface of the prosthesis according to the invention have a taper in the longitudinal direction, or, in other words, a slight conicity between the end embedded in the bone and that end which, as the case may be, must be taken hold of for the extraction of the prosthesis. The advantageous results o the invention are obtained with conicities of relatively low value.

The invention is applicable to all kinds of metal implants capable of acting as prostheses or used in the treatment of bones. Particularly interesting results are obtained in the case of prostheses of the hip or knee and, in a general way, any prosthesis including a part in the shape of a stem. Such a stem may be rectilinear or have a certain curvature, so that it may better match the shape of the bone in which it is intended to be anchored. Further, the outer surface of the stem is not necessarily in the shape of a regular cylinder. It is even in many cases advantageous, in particular in order to satisfy requirements of the strength of materials, to shape the stem so as to give it a progressively increasing thickness, at least in its upper part. Some of the splines extend throughout the length of the stem and some others may, if they extend from the upper part, lead to an edge of the stem without extending to its end.

In another aspect, the invention provided a method for producing a splined prosthesis element by the general lost wax investment casting technique, comprising constructing a wax pattern of the element to be produced, effecting a refractory moulding on said pattern so as to constitute a mould, and casting liquid metal in said mould so as to produce the desired element. Before the refractory moulding, there are placed in position in the flutes of the wax pattern, rods which have a cross-sectional profile corresponding to that of the spline of the final element and which have a slight conicity from one end to the other so as to produce, after the casting of the metal in the refractory mould, an element with tapering splines.

In the case, for example, of a prosthesis element having a stem, the stem is first made in wax in the dimensions of the element to be reproduced by providing on the periphery of the stem concave grooves parallel to the axis. In addition, rods are made for example from polystyrene or wax, which have the length of the splines to be produced and a slight conicity from one end to the other. The cross-sectional profile of the rods corresponds to that of the splines of the final element. These rods are assembled, in particular by adhesion, in the concave grooves of the stem. In this way a wax pattern of the element to be produced is constructed. This wax pattern is then provided with a refractory covering in the known manner so as to form a refractory mould and the final element is produced by casting liquid metal in such a mould from which all the wax was previously removed.

In another aspect, which corresponds to a preferred manner of carrying out the invention, the invention provides a method for producing a splined prosthesis element, comprising constructing by the known general lost wax investment casting technique a smooth metal blank which is slightly oversized relative to the transverse dimensions of the element to be produced, treating said blank in succession by hot forging, then by cold forging, until the final dimensions of the desired element are obtained, and forming on said element by an electromachining tapered longitudinal splines having the desired cross-sectional profile.

Such a method comprises first producing by the lost wax investment casting technique a pattern of an element, for example a stem, which has a smooth outer surface and includes a slight extra allowance relative to the transverse dimensions of the element to be obtained. By way of a concrete example, in respect of a stem, of about 15 mm in diameter, an extra allowance of 1 mm per surface is suitable. The as-cast blast blanks are then hot-forged so as to produce an intermediate element which still has a slight extra allowance (in the foregoing dimensioned example, this may be about 0.50 mm). The final calibration giving the final dimensions is effected by cold forging. With this forged stem having a smooth outer surface, the splines are produced by removing metal with the electromachining technique. For this purpose, a tool is used which is shifted in the longitudinal direction of the stem so as to cut the splines therein. The machining may be effected by successive passes with tools having different profiles. In a modification which is preferred from the economical point of view, a single tool is used in one pass so as to produce the desired cross-sectional profile of the splines, namely a profile having an optimum retaining effect on the bone tissue when the latter develops or grows.

The method just described is the most interesting in practice. Indeed, in starting with an as-cast blank, the hot and cold-forging steps very substantially improve the mechanical properties of the element. The electromachining technique wholly respects the mechanical properties and may be carried out with conventional equipment which merely need to include a tool satisfying the requirements of the invention.

BRIEF DESCRIPTION OF THE DRAWINGS

The invention will now be illustrated, without in any way being limited, by the following description which concerns a prosthesis adapted to be inserted into the femur (prosthesis of the hip), with reference to the accompanying drawings in which.

DETAILED DESCRIPTION OF THE PREFERRED EMBODIMENT

Figure 1:
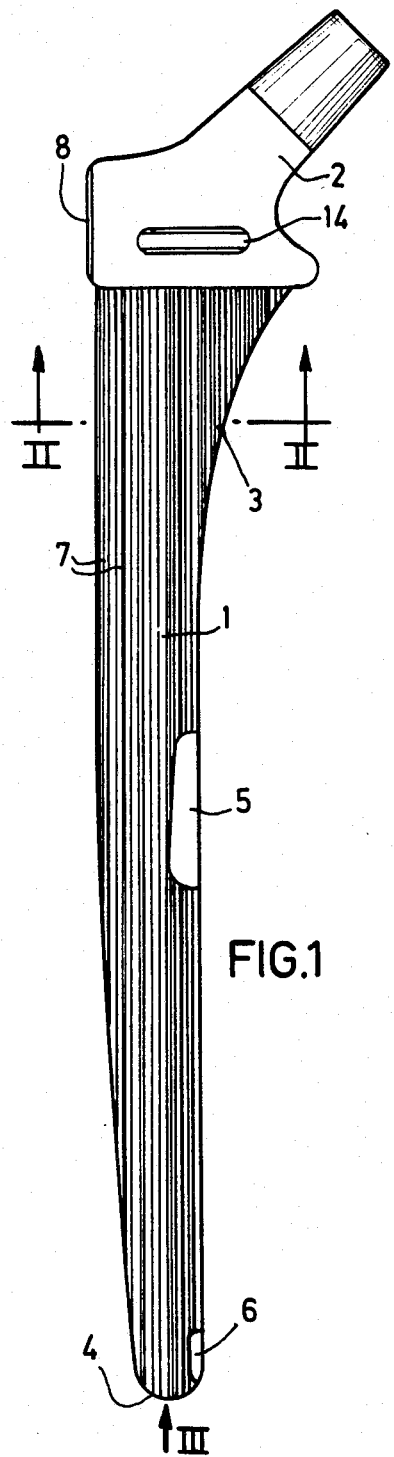
FIG. 1 is a front elevational view of the prosthesis.
Figure 2:
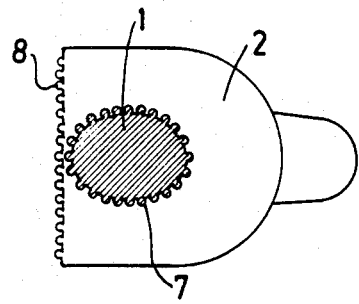
FIG. 2 is a sectional view taken along line II—II of FIG. 1.

FIGS. 1 and 2 show diagrammatically a prosthesis element adapted to be inserted into the femur. Generally, it comprises two parts, a stem 1 and a part 2 which, for the sake of convenience, will be termed "neck". In the chosen example, the stem 1 has a length of about 200 mm and a transverse dimension of approximately 15 mm. FIG. 2 shows more clearly, in section, the slightly elliptical shape of the stem 1. The end 4 is the end which is the most deeply embedded into the bone of the femur. The end 3 is shaped as shown in FIG. 1 so as to afford maximum strength. The stem 1 also includes cavities two of which, 5, 6 are shown.

Figure 4:
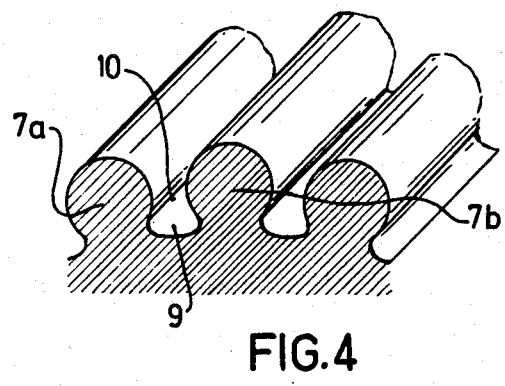
FIG. 4 is the cross-sectional profile of a spline to an enlarged scale.
Figure 5:
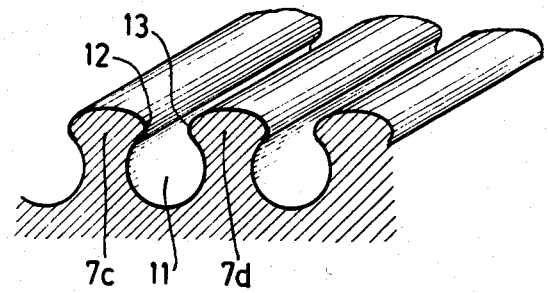
FIG. 5 is similar to FIG. 4, showing a modification of the profile.

According to the invention, the stem 1 has splines or flutes 7. Some of the latter, in particular in the median part, extend throughout the length of the stem 1. Other splines, in particular in the vicinity of the upper part 3 or of the cavities 5, 6, do not extend to the end 4 but stop at the corresponding outer edge of the stem. It is also clear from FIGS. 1 and 2 that a part 8 of the neck in the extension of the stem 1 is also splined. This part 8 is restricted to one face of the neck 2. An essential feature of the invention is that the splines 7, 8, have a cross-sectional profile which is capable of effectively retaining the bone tissue when it develops or grows after the insertion of the prosthesis. FIGS. 4 and 5 show examples of suitable profiles. In FIG. 4 there are seen two adjacent splines 7a, 7b defining there between a trough 9 or inner spline surface. It can be seen in FIG. 4 that the inner surface or trough 9 is defined by a curve which outwardly tapers as indicated at 10 before diverging to form the spline proper thereby providing a "neck" for the trough 9.

It is the conformation of the interior surface which ensures the anchoring effect and the bone tissue retaining capability. It will be understood that the drawing in FIG. 4 has been highly magnified (magnification about ten times).

FIG. 5 shows a modification with two adjacent splines 7c, 7d. The spline bottom or hollow 11 has two bosses 12, 13 approaching each other in the upper part. In this case also, the desired retaining effect is ensured.

Figure 3:
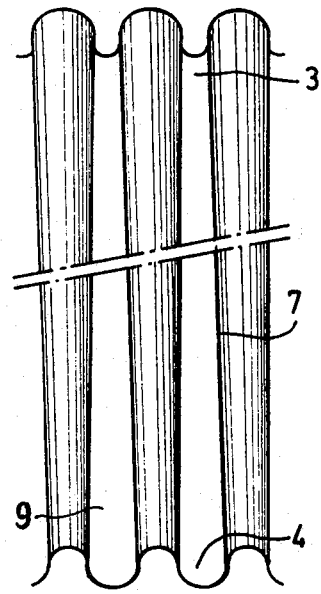
FIG. 3 is a view of the interior or hollow of a spline in the direction of arrow III of FIG. 1.

According to another fundamental feature of the invention which is combined with that concerning the cross-sectional profile of the plane, the longitudinal profile of the latter is not cylindrical but, on the contrary tapered. As illustrated in FIG. 3, the inner surface of a spline 7 tapers from the end 4 the most deeply embedded in the bone to the end 3 in the vicinity of the neck 2. It will be understood that the representation of FIG. 3 is diagrammatic. In practice, with the aforementioned stem dimensions (namely: length 200 mm, diameter 15 mm) the transverse dimension of a spline hollow in the vicinity of the end 4 is for example 1.5 mm while it is 1.3 mm in the vicinity of the end 3. This downwardly divergent profile enables the prosthesis to be extracted if required.

For the purpose of the extraction, a pair of recesses 14 (see FIG. 1) may be provided on the neck 2 to enable the surgeon to insert a tool for extracting the prosthesis.

Figure 6:
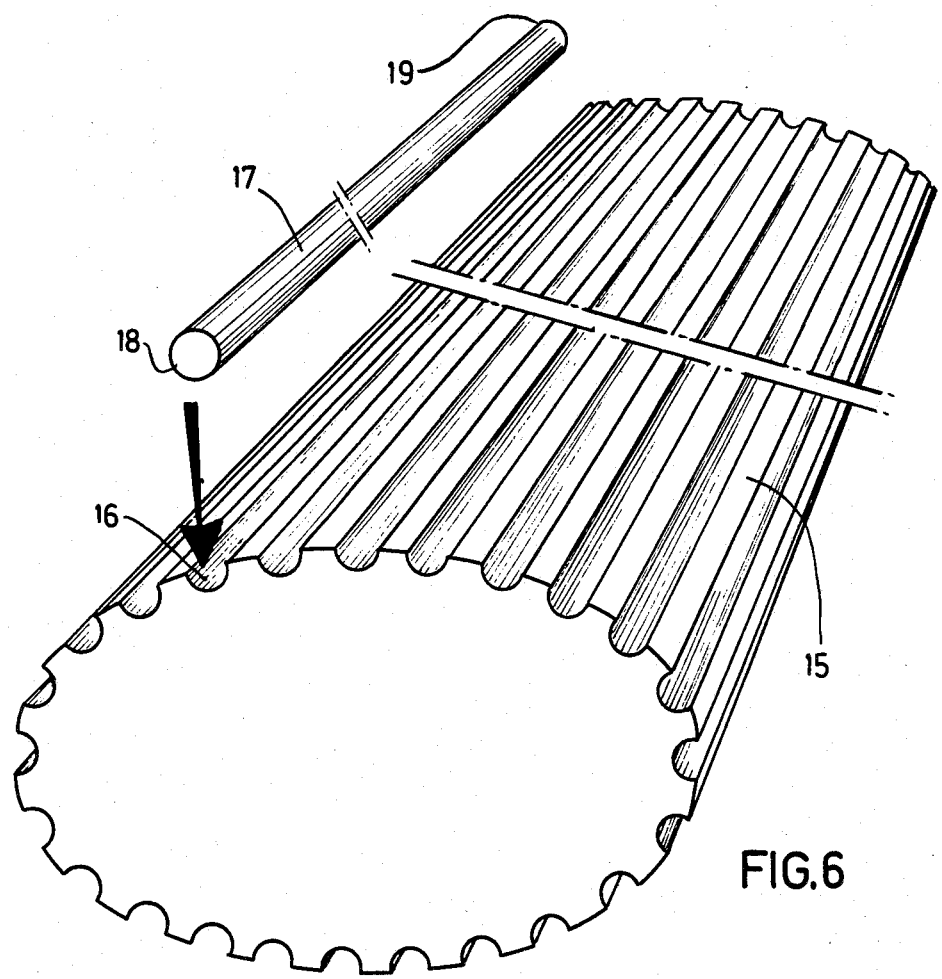
FIG. 6 is a diagram illustrating a method for producing the prosthesis according to the invention.

FIG. 6 diagrammatically illustrates a method for producing a prosthesis stem of the type shown in FIGS. 1 to 5. This method employs the general lost wax investment casting technique. FIG. 6 shows the stem 15 of wax which is made with the dimensions of the element to be produced. It has throughout its periphery concave grooves 16 parallel to the general axis of the stem 15.

Rods 17 of polystyrene or wax are constructed which have a cross-sectional profile similar to the splines of FIGS. 4 and 5 and a tapering longitudinal profile. Thus their diameter at the end 18 is larger than that at the end 19. These rods are individually placed in position by adhesion in the concave grooves 16 of the wax stem. The wax pattern obtained in accordance with the illustration of FIG. 6 is then covered with a refractory material in the known manner. Liquid metal may be cast in the refractory mould to produce the final prosthesis element.

Figure 7:
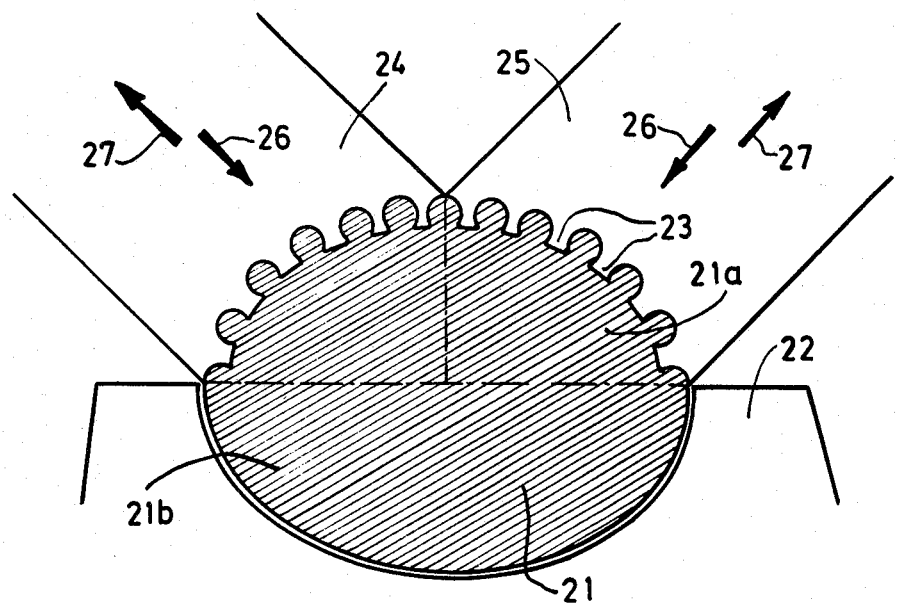
FIGS. 7 and 8 are diagrams illustrating another preferred embodiment for producing the prosthesis according to the invention.

It is preferred to produce the prosthesis according to the invention by a method in which there is first of all produced by the lost wax investment casting technique a stem pattern whose outer surface is smooth and whose transverse dimensions are slightly increased relative to those of the final element to be obtained. With the aforementioned figures (length of the stem 200 mm and diameter 15 mm) the extra allowance on the wax pattern may be about 1 mm on each side, namely 2 mm in all. A metal stem blank is then made with such an extra allowance. The blank is then hot-forged to produce an intermediate element having less extra allowance, for example about 0.50 mm per side relative to the final element. The final calibration is achived by cold-forging which considerably improves the mechanical properties of the prosthesis. The splined final shape of the prosthesis according to the invention is obtained by removing metal by an electromachining technique. The latter is diagrammatically illustrated in FIGS. 7 and 8. FIG. 7 shows in section the stem 21 of the prosthesis to be produced. The latter is held horizontally in a fixing tool 22 which leaves exposed only the upper half 21a of the stem 21. The longitudinal grooves or spline hollows 23 are obtained by the use of a pair of electrodes 24, 25. The active end of each electrode covers one-half of the upper part 21a of the stem so that this upper part 21a is completely covered by the electrodes, as shown in FIG. 7. For the purposes of the electro-erosion or electro-machining, the electrodes 24, 25 approach the part 21a (arrows 26) in a converging motion, after which the two electrodes are withdrawn (arrows 27). The element (stem 21) is then turned round and the same operation is carried out on the other half 21b.

Figure 8:
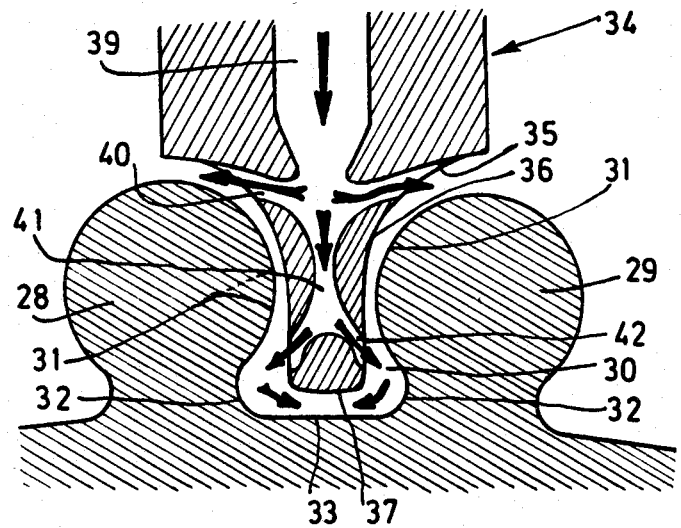

FIG. 8 shows to an enlarged scale the constitution of an electrode element 24, 25. There are seen two adjavent splines 28, 29, separated by a groove or spline hollow 30. In the chosen example, the groove 30 has a profile resulting from the combination of arcs of a circle 31 and 32 of opposite curvature. The bottom of the groove is formed by a flat surface 33.

The element 34 of the electrode, which is made from copper, is designed to machine the profile 31, 32, 33 and comprises for theis purpose arcuate parts 35, 36 and an end part 37. Inner passages are provided in the electrode element 34 to permit the passage of an electrolyte as shown by the arrows in FIG. 8. Thus it can be seen that the element 34 has a main passage 39, two lateral passages 40, an axial passage 41, and two other lateral passages 42. Owing to the shape of the electrode element 34 and to the circulation of the electrolyte (which may be brine), the metal of the prosthesis stem is removed in accordance with the profile desired for the groove 30 between the splines 28, 29 both in the transverse direction and in the longitudinal direction of this groove.

It will be understood that the production methods described hereinbefore merely constitute examples. A person skilled in the art will understand that modifications may be envisaged in particular to adapt the production method to the type of the material of the prosthesis.

Thus the rough prosthesis element or blank may also be obtained by hot-forging a cylindrical bar of suitable dimensions. The hot-forging requires a number of passes which depends on the type of material. Subsequent to the forging, an element is obtained which has high mechanical properties.

The foregoing techniques are most suitable for stainless steels such as chrome-cobalt steels, for example that of the grade HS21. It will be understood that other materials may be employed and in particular other metal alloys.

We claim:

1. An osteal prosthesis comprising:
   an elongate stem for insertion and fixing in bone;
   means at a proximal end of said stem for permitting said stem to be inserted in bone by initial insertion in said bone of a distal end of said stem opposite said proximal end; and spline means on said stem and extending generally in the direction of elongation of said stem, said spline means comprising:
 (a) a plurality of raised spline elements tapered so as to have increased width towards said proximal end, and
 (b) a plurality of troughs defined between said spline elements, said troughs being tapered so as to have increased width towards said distal end, wherein the cross-sectional profiles of said spline elements and troughs is such that said spline elements and troughs impart a bone tissue retaining capability and said prosthesis is capable of being extracted from the bone by tractive movement.

2. A prosthesis according to claim 1 wherein the cross-sectional profile of at least some of the spline elements is such as to define at least partly a narrowed part in an adjacent said trough.

3. A prosthesis according to claim 2, wherein said spline element cross-sectional profile is curvilinear.

4. A prosthesis according to claim 2, wherein said spline element cross-sectional profile is circular.

5. A prosthesis according to claim 2, wherein said spline element cross-sectional profile has a combination of circular and noncircular curvilinear portions.

6. A prosthesis according to claim 5 including rectilinear portions of said spline element cross-sectional profile interconnecting said curvilinear and circular portions.

* * * * *